United States Patent
Degrenne et al.

(10) Patent No.: US 10,495,681 B2
(45) Date of Patent: Dec. 3, 2019

(54) SYSTEM AND METHOD FOR DETERMINING IF DETERIORATION OCCURS IN INTERFACE OF SEMICONDUCTOR DIE OF ELECTRIC POWER MODULE

(71) Applicant: MITSUBISHI ELECTRIC CORPORATION, Tokyo (JP)

(72) Inventors: Nicolas Degrenne, Rennes (FR); Stefan Mollov, Rennes (FR)

(73) Assignee: MITSUBISHI ELECTRIC CORPORATION, Tokyo (JP)

(*) Notice: Subject to any disclaimer, the term of this patent is extended or adjusted under 35 U.S.C. 154(b) by 70 days.

(21) Appl. No.: 15/741,070

(22) PCT Filed: Aug. 23, 2016

(86) PCT No.: PCT/JP2016/075109
§ 371 (c)(1),
(2) Date: Dec. 29, 2017

(87) PCT Pub. No.: WO2017/043346
PCT Pub. Date: Mar. 16, 2017

(65) Prior Publication Data
US 2018/0188309 A1    Jul. 5, 2018

(30) Foreign Application Priority Data
Sep. 8, 2015 (EP) .................... 15184254

(51) Int. Cl.
*G01R 31/04* (2006.01)
*G01N 29/14* (2006.01)
*G01N 29/04* (2006.01)

(52) U.S. Cl.
CPC .......... *G01R 31/046* (2013.01); *G01N 29/04* (2013.01); *G01N 29/14* (2013.01); *G01N 2291/2697* (2013.01)

(58) Field of Classification Search
CPC ....... H01L 21/00; H01L 2221/00; H03H 1/00; H03H 2210/00; H02J 1/00
See application file for complete search history.

(56) References Cited

U.S. PATENT DOCUMENTS

| 6,384,610 B1 * | 5/2002 | Wilson .................. G01N 17/02 324/663 |
| 2003/0024298 A1 | 2/2003 | Baber et al. |

(Continued)

FOREIGN PATENT DOCUMENTS

JP    2014-180089 A    9/2014

OTHER PUBLICATIONS

Preliminary Notice of Reasons for Rejection issued in related JP Application No. 2017-557227 dated Sep. 20, 2018.

*Primary Examiner* — Huy Q Phan
*Assistant Examiner* — Temilade S Rhodes-Vivour
(74) *Attorney, Agent, or Firm* — Birch, Stewart, Kolasch & Birch, LLP

(57) ABSTRACT

The present invention concerns a system for determining if a deterioration occurs in an interface of a semiconductor die of an electric power module, the electric power module further comprising a substrate and at least one electromechanical transducer, the semiconductor die and the at least one electromechanical transducer being placed on or embedded within the substrate, wherein the system comprises: —means for transferring at least one electric signal to the at least one electromechanical transducer, —means for measuring the impedance of the at least one electromechanical transducer, —means for comparing the impedance of the at least one electromechanical transducer to a predeter- (Continued)

mined value, —means for deciding that the deterioration occurs in the interface of the semiconductor die according to the comparison result.

12 Claims, 5 Drawing Sheets

(56) References Cited

U.S. PATENT DOCUMENTS

| | | | |
|---|---|---|---|
| 2003/0076232 A1* | 4/2003 | Sato | H02M 7/00 340/679 |
| 2007/0062299 A1* | 3/2007 | Mian | G07C 3/00 73/763 |
| 2007/0164632 A1* | 7/2007 | Adachi | A61B 8/4483 310/311 |
| 2008/0319692 A1 | 12/2008 | Davis et al. | |
| 2009/0284263 A1 | 11/2009 | Kirkelund et al. | |
| 2009/0322557 A1* | 12/2009 | Robb | G01M 5/0033 340/870.3 |
| 2014/0221841 A1* | 8/2014 | Okuda | A61B 8/4444 600/459 |
| 2014/0265720 A1* | 9/2014 | El-Gamal | B06B 1/0292 310/300 |

* cited by examiner

SYSTEM AND METHOD FOR DETERMINING IF DETERIORATION OCCURS IN INTERFACE OF SEMICONDUCTOR DIE OF ELECTRIC POWER MODULE

TECHNICAL FIELD

The present invention relates generally to a method and system for determining if a deterioration occurs in an interface of a semiconductor die of an electric power module.

BACKGROUND ART

Electric power modules are composed of one or plural dies which are placed on a substrate and interconnected to the substrate through interfaces.

During the operating of the electric power module, interfaces are subject to stresses that may generate deteriorations such as cracks or disintegrations of the soldering materials.

Deteriorations degrade the structure of the electric power module and reduce the operating life time of the electric power module.

A sudden break of the electric power module may interupt the operation of the device in which the electric power module is embedded.

For example, if the electric power module is embedded in an offshore windmill, it will be helpful to monitor the health of the electric power module in order to plan the maintenance of the offshore windmill.

The same arises when the electric power module is embedded in a train.

SUMMARY OF INVENTION

The present invention aims at detecting an apparition of a failure in the structure of a electric power semiconductor in order to notify deteriorations in interfaces of electric power modules.

To that end, the present invention concerns a system for determining if a deterioration occurs in an interface of a semiconductor die of an electric power module, the electric power module further comprising a substrate and at least one electromechanical transducer, the semiconductor die and the at least one electromechanical transducer being placed on or embedded within the substrate, wherein the system comprises:

means for transferring at least one electric signal to the at least one electromechanical transducer,
means for measuring the impedance of the at least one electromechanical transducer,
means for comparing the impedance of the at least one electromechanical transducer to a predetermined value,
means for deciding that the deterioration occurs in the interface of the semiconductor die according to the comparison result.

The present invention concerns also a method for determining if a deterioration occurs in an interface of a semiconductor die of an electric power module, the electric power module further comprising a substrate and at least one electromechanical transducer, the semiconductor die and the at least one electromechanical transducer being placed on or embedded within the substrate, wherein the method comprises the steps of:

transferring at least one electric signal to the at least one electromechanical transducer,
measuring the impedance of the at least one electromechanical transducer,
comparing the impedance of the at least one electromechanical transducer to a predetermined value,
deciding that the deterioration occurs in the interface of the semiconductor die according to the comparison result.

Thus, the apparition and the propagation of a deterioration in an interface of a semiconductor die can be detected.

According to a particular feature, the at least one electric signal is transferred to the at least one electromechanical transducer plural consecutive times and the system further comprises means for performing statistics on measured impedances and to disable the comparing and if statistics show a high level of discrepancies.

Thus, the result of the deterioration detection can be ignored if it is not reliable enough.

According to a particular feature, if statistics show a high level of discrepancies, the system comprises means for indicating the unreliablity of the measurement.

According to a particular feature, the electric power module further comprises a waveguide between the electromechanical device and one semiconductor die.

Thus, the coupling between the electromechanical sensor and a die interface is improved.

According to a particular feature, the electric power module comprises plural semiconductor dies and a single electromechanical transducer and the at least one electric signal is transferred to the single electromechanical transducer.

Thus, a single electromechanical sensor is used to monitor the interfaces of several dies.

According to a particular feature, the electric power module comprises plural semiconductor dies and one electromechanical transducer for each semiconductor die and at least one electric signal is transferred sequentially to each electromechanical transducer, the impedance of each electromechanical transducer is measured and, each measured impedance being compared to one predetermined value and the deciding that the deterioration occurs in one interface is performed according to the comparison result.

Thus, each die interface is monitored separately and it is possible to locate the deterioration location.

According to a particular feature, the plural signals at different frequencies covering a frequency range are transferred to the or each electromechanical transducer, the impedance of the or each electromechanical transducer is measured at each frequency.

Thus, it is possible to detect the influence of the deterioration on one or several frequencies.

According to a particular feature, only the real part of the impedance is used for the comparison.

Thus, the capacitive or/and inductive behaviour of the electromechanical sensor can be discarded and the result is more sensitive to the presence of a change in the mechanical structure of the electric power module.

According to a particular feature, the comparison is performed using a quadratic distance comparison or a cross-correlation function, or a mean absolute percentage deviation function, or a covariance change function.

Thus, it is possible to calculate a distance between the pre-determined value and the measured value, and it is possible to evaluate the presence and the size of a deterioration in an interface.

According to a particular feature, the means for deciding that the deterioration occurs in the interface of the semiconductor die according to the comparison result further determines a remaining lifetime of the electric power module.

Thus, it is possible to avoid failure and to realize just-in-time proactive maintenance to optimize life-cycle cost of the device.

According to a particular feature, the remaining lifetime is computed using a linear extrapolation of the deterioration mathematical distance between the predetermined and the measured impedance values evolution through time and by computation of the crossing point between the extrapolation and a distance threshold.

Thus, the end of life can be evaluated easily from several measurements.

The characteristics of the invention will emerge more clearly from a reading of the following description of example embodiments, the said description being produced with reference to the accompanying drawings, among which:

DESCRIPTION OF EMBODIMENTS

Figure 1A:
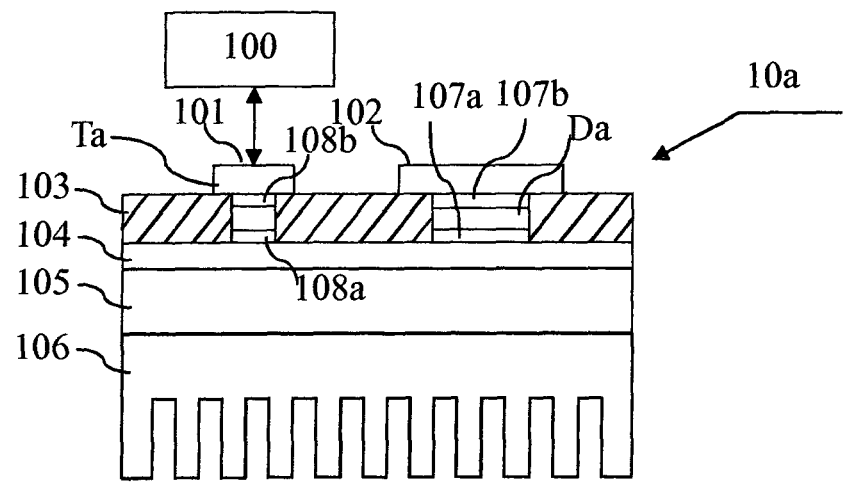
FIG. 1a represents a first example of an architecture of a system for monitoring deteriorations in at least one interface of an electric power module comprising at least one die.

FIG. 1a represents a first example of an architecture of a system for monitoring deteriorations in at least one interface of an electric power module comprising at least one die.

The system for monitoring deteriorations in at least one interface of an electric power module comprising at least one die is composed of a deterioration monitoring device 100 and an electric power module 10a.

The electric power module 10a is composed of a die Da and an electromechanical transducer Ta. The die Da and the electromechanical transducer Ta are embed in a printed circuit board 103 (PCB). For example, the PCB has an FR-4 grade designation. FR-4 is a composite material composed of woven fiberglass cloth with an epoxy resin binder.

The die Da has a first interconnection 107b to the substrate metallization 102. The interconnection 107b and the metallization 102 are a first interface of the Die Da. The metallization 102 is for example composed of copper. The interconnection 107b is for example realized by soldering or sintering. Deterioration may occur either in the metallization 102 or the interconnection 107b.

The lower side of the PCB 103 is a second substrate metallization 104.

The interconnection 107a and the metallization 104 are a second interface of the Die Da. The metallization 104 is for example composed of copper. The interconnection 107a is for example realized by soldering or sintering. Deterioration may occur in the metallization 104 and/or the interconnection 107a. The electromechanical transducer Ta is connected to the substrate metallization 101 through an interconnection 108b.

The electromechanical transducer Ta is connected to the substrate metallization 104 through an interconnection 108a.

The metallizations 101 and 104 are for example composed of copper and are connected electrically and mechanically to Ta via the interconnections 108a and 108b. Typically the electromechanical transducer Ta is soldered or sintered to the metallizations 101 and 104.

The electromechanical transducer Ta may be also attached to the substrate 103 using a mechanical adhesive, such as glue, screw, spring, solder or sintered. The electromechanical transducer Ta may be embedded in viscous liquid and is in the example of FIG. 1a embedded within the PCB 103.

For example, the electromechanical transducer Ta is attached on the substrate of the electric power module with the same process than the die Da itself and is located in the vicinity of the die Da like for example at less than one cm from the die Da.

The electric power module 10a comprises a base plate 105 on which the PCB is mounted and a heat sink 106.

The electromechanical transducer Ta is connected to the deterioration monitoring device 100 through the metallizations 101 and 104.

The electromechanical transducer Ta is a sub-assembly that maps conformally the electrical and mechanical characteristics at its electrical and mechanical interfaces within a given frequency range. The electromechanical transducer Ta may be of different kinds.

The electromechanical transducer Ta may be a sub-assembly composed of at least an electrostrictive material. A piezoelectric device such as a ceramic capacitor is one example of such a sub-assembly.

The electromechanical transducer Ta may be a sub-assembly composed of at least a magnetostrictive material. An inductor composed of a magnetizing coil and a magnetostrictive ferromagnetic material is one example of such sub-assembly.

The electromechanical transducer Ta may be a dedicated micro electromechanical system.

Figure 1B:
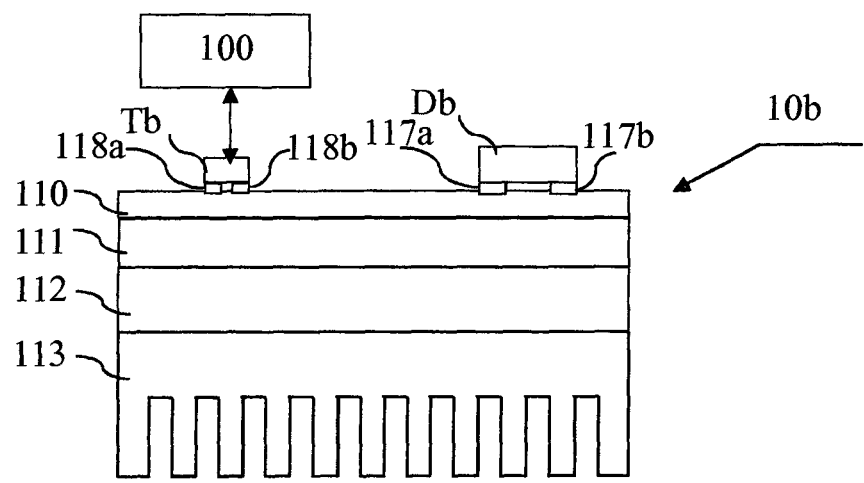
FIG. 1b represents a second example of an architecture of a system for monitoring deteriorations in at least one interface of an electric power module comprising at least one die.

FIG. 1b represents a second example of an architecture of a system for monitoring deteriorations in at least one interface of an electric power module comprising at least one die.

The system for monitoring deteriorations in at least one interface of an electric power module comprising at least one die is composed of a deterioration monitoring device 100 and an electric power module 10b.

The electric power module 10b is composed of a die Db and an electromechanical transducer Tb. The die Db and the electromechanical transducer Ta are placed on a substrate 111, the surface of which comprises a metallization layer 110. For example, the PCB has an FR-4 grade designation or is composed of ceramic.

The die Db has a first interconnection 117*b* to the substrate metallization 110. The interconnection 117*b* and the metallization 110 are a first interface of the Die Db. The metallization 110 is for example composed of copper. The interconnection 117*b* is for example realized by soldering or sintering. Deterioration may occur either in the metallization 110 or the interconnection 117*b*.

The interconnection 117*a* and the metallization 110 are a second interface of the Die Db. The metallization 110 is for example composed of copper. The interconnection 117*a* is for example realized by soldering or sintering. Deterioration may occur in the metallization 110 and/or the interconnection 117*a*.

The electromechanical transducer Tb is connected to the substrate metallization 110 through interconnections 118*a* and 108*b*.

The metallization 101 is for example composed of copper and is connected electrically and mechanically to Tb via the interconnections 118*a* and 118*b*. Typically the electromechanical transducer Tb is soldered or sintered to the metallization 110.

The electromechanical transducer Tb may be also attached to the substrate 111 using a mechanical adhesive, such as glue, screw, spring, solder or sintered. The electromechanical transducer Tb may be embedded in viscous liquid.

For example, the electromechanical transducer Tb is attached on the substrate 110 of the electric power module 10*b* with the same process than the die Db itself and is located in the vicinity of the die Db like for example at less than one cm from the die Da.

The electric power module 10*b* comprises a base plate 112 on which the substrate 111 is mounted and a heat sink 113.

The electromechanical transducer Tb is connected to the deterioration monitoring device 100 through the metallization 110.

The electromechanical transducer Tb is a sub-assembly that maps conformally the electrical and mechanical characteristics at its electrical and mechanical interfaces within a given frequency range. The electromechanical transducer Tb may be of different kinds.

The electromechanical transducer Tb may be a sub-assembly composed of at least an electrostrictive material. A piezoelectric device such as a ceramic capacitor is one example of such a sub-assembly.

The electromechanical transducer Tb may be is a sub-assembly composed of at least a magnetostrictive material. An inductor composed of a magnetizing coil and a magnetostrictive ferromagnetic material is one example of such sub-assembly.

The electromechanical transducer Ta may be a dedicated micro electromechanical system.

Figure 2A:
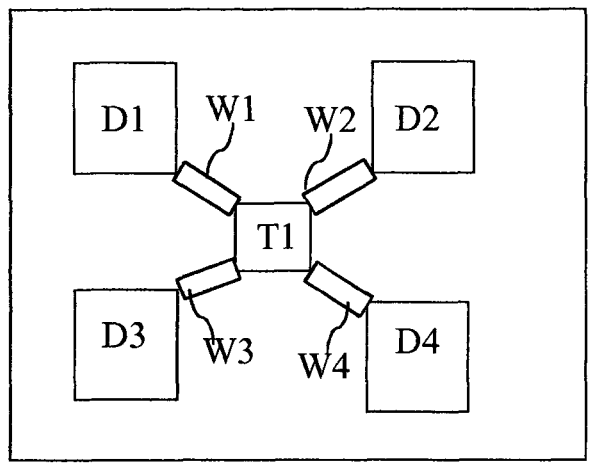
FIG. 2a represents a first example of a topology of an electric power module comprising electromechanical transtuctors according to the present invention.

FIG. 2*a* represents a first example of a topology of an electric power module comprising electromechanical transtuctors according to the present invention.

In the example of FIG. 2*a*, one electromechanical transducer T1 monitors deteriorations on interfaces of a plurality of dies D1 to D4.

The electromechanical transducer T1 is located in the vicinity of the dies D1 to D4.

In order to improve the propagation of the vibrations of the electromechanical transducer T1, waveguides W1 to W4 are respectively provided between the electromechanical transducer T1 and each die D1 to D4. Waveguides W1 to W4 improve the mechanical coupling between the electromechanical transducer T1 and the dies D1 to D4.

Figure 2B:
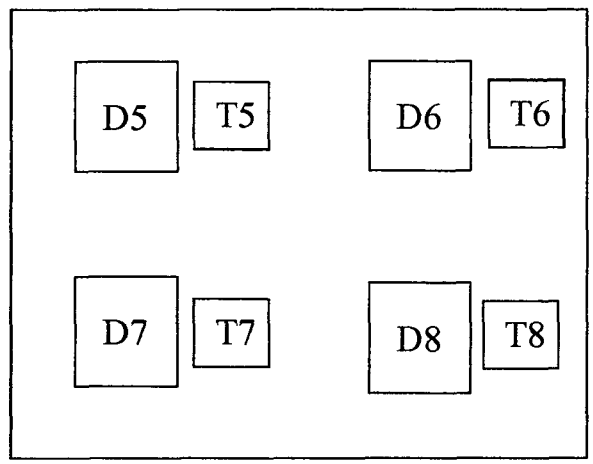
FIG. 2b represents a second example of a topology of an electric power module comprising electromechanical transducers according to the present invention.

FIG. 2*b* represents a second example of a topology of an electric power module comprising electromechanical transducers according to the present invention.

In the example of FIG. 2*b*, one electromechanical transducer monitors deteriorations on interfaces of one die.

The electromechanical transducer T5 monitors deteriorations on interfaces of the die D5, the electromechanical transducer T6 monitors deteriorations on interfaces of the die D6, the electromechanical transducer T7 monitors deteriorations on interfaces of the die D7 and the electromechanical transducer T8 monitors deteriorations on interfaces of the die D6, the electromechanical transducer T8.

Figure 3:
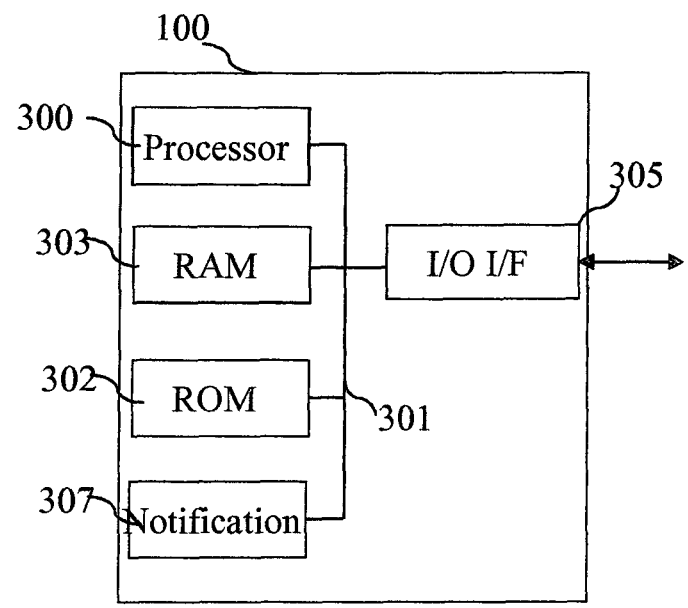
FIG. 3 represents an example of the architecture of a deterioration monitoring device according to the present invention.

FIG. 3 represents an example of the architecture of a deterioration monitoring device according to the present invention.

Figure 6:
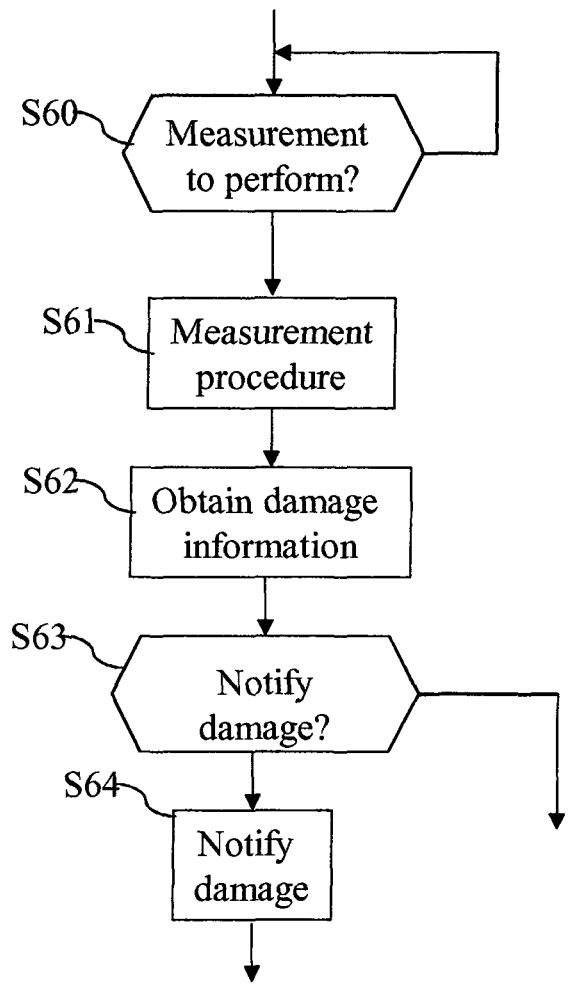
FIG. 6 represents an example of an algorithm executed by the deterioration monitoring device according to the present invention.

The deterioration monitoring device 100 has, for example, an architecture based on components connected together by a bus 301 and a processor 300 controlled by a program as disclosed in FIG. 6.

The bus 301 links the processor 300 to a read only memory ROM 302, a random access memory RAM 303, an input output I/O IF interface 305 and notification means 307.

The memory 303 contains registers intended to receive variables and the instructions of the program related to the algorithm as disclosed in FIG. 6.

The processor 300 generates at least one signal at a given frequency or generates plural signals at different frequencies through the input output I/O IF 305 and receives in response to the generated signal, a voltage and a current measurements in order to be able to determine the impedance of the electromechanical sensor at each frequency.

The processor 300, may command the notification means 307 in order to notify the level of damage of the electric power module or may command the notification means 307 in order to notify a lifetime expectation of the electric power module.

The read-only memory, or possibly a Flash memory 302, contains instructions of the program related to the algorithm as disclosed in FIG. 6, when the deterioration monitoring device 100 is powered on, to the random access memory 303.

The notification means may be 307 a light indicator or information indicating an expected remaining life of the electric power module. Notification means may comprise communication means which transfer information related the monitored electric power module.

The deterioration monitoring device 100 may be implemented in software by execution of a set of instructions or program by a programmable computing machine, such as a PC (Personal Computer), a DSP (Digital Signal Processor) or a microcontroller; or else implemented in hardware by a machine or a dedicated component, such as an FPGA (Field-Programmable Gate Array) or an ASIC (Application-Specific Integrated Circuit).

In other words, the deterioration monitoring device 100 includes circuitry, or a device including circuitry, causing the deterioration monitoring device 100 to perform the program related to the algorithm as disclosed in FIG. 6.

Figure 4A:
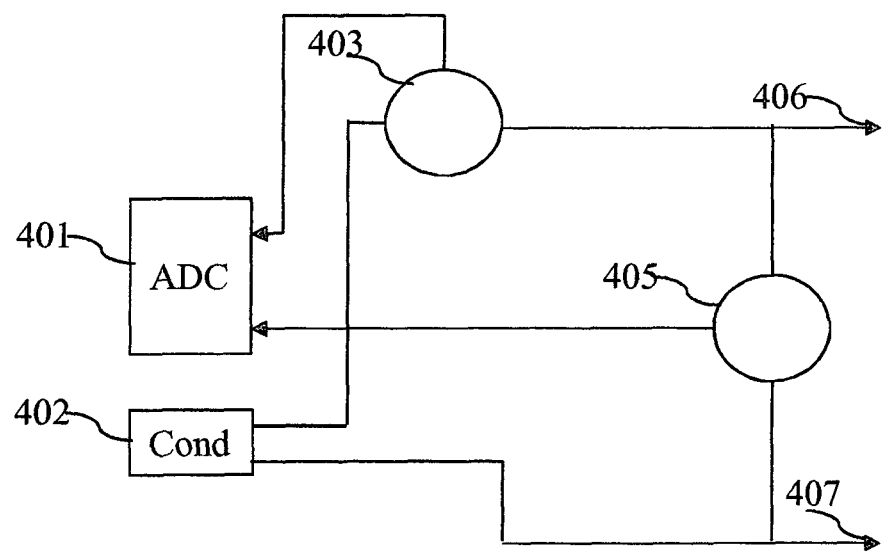
FIG. 4a represents an example of the architecture of the input output interface of the deterioration monitoring device in the first example of topology of an electric power module.

FIG. 4*a* represents an example of the architecture of the input output interface of the deterioration monitoring device in the first example of topology of an electric power module.

The input output interface 305 comprises a signal conditioner Cond 402.

The signal conditioner 402 may be an oscillator, the frequency of which may be modified or an amplifier which amplifies an analogue or digital signal provided by the processor 300 or a filter which removes harmonics of a digital signal provided by the processor 300.

The signal provided by the signal conditioner 402 is fed to the electromechanical transducer T which terminals are connected to 406 and 407.

The input output interface 305 comprises a current sensor 403 which measures the current of the signal provided by the signal conditioner 402 to the electromechanical transducer T.

The input output interface 305 comprises a voltage sensor 405 which measures the voltage of the signal provided by the signal conditioner 402 to the electromechanical transducer T.

The sensed current and voltage are provided to an analogue to digital converter ADC 401.

Figure 4B:
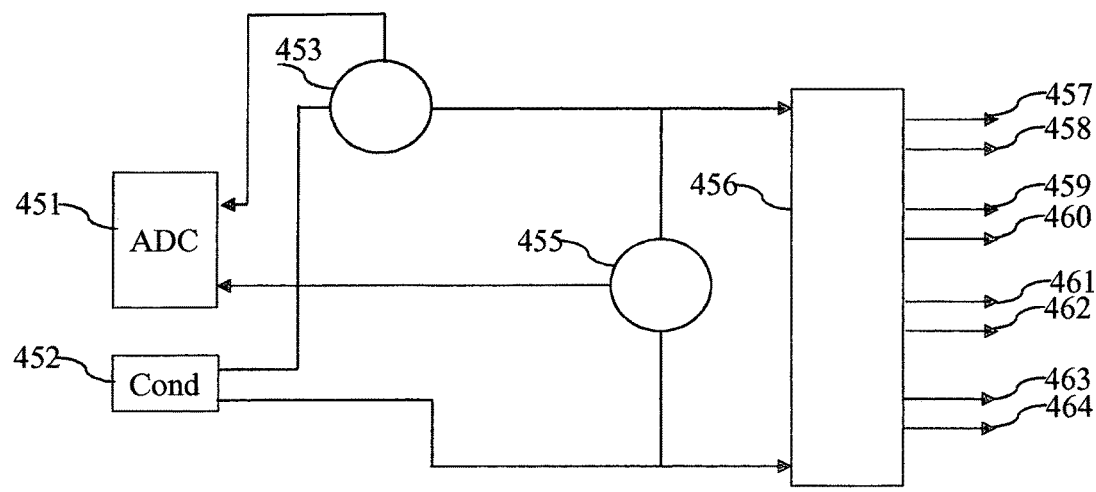
FIG. 4b represents an example of the architecture of the input output interface of the deterioration monitoring device in the second example of topology of an electric power module.

FIG. 4*b* represents an example of the architecture of the input output interface of the deterioration monitoring device in the second example of topology of an electric power module.

The input output interface 305 comprises a signal conditioner Cond 452.

The signal conditioner 452 may be an oscillator, the frequency of which may be modified or an amplifier which amplifies an analogue or digital signal provided by the processor 300 or a filter which removes harmonics of a digital signal provided by the processor 300.

The signal provided by the signal conditioner 452 is fed to a multiplexer 456.

The multiplexer 456 provides the signal outputted by the signal conditioner 452 sequentially to each of the electromechanical transducers T5 to T8 according to commands generated by the processor 300.

The signal provided by the multiplexer 456 is fed to the electromechanical transducer T5 which terminals are connected to 457 and 458.

The signal provided by the multiplexer 456 is fed to the electromechanical transducer T6 which terminals are connected to 459 and 460.

The signal provided by the multiplexer 456 is fed to the electromechanical transducer T7 which terminals are connected to 461 and 462.

The signal provided by the multiplexer 456 is fed to the electromechanical transducer T8 which terminals are connected to 463 and 464.

The input output interface 305 comprises a current sensor 453 which measures the current of the signal provided by the signal conditioner 452 to the electromechanical transducers T5 to T8.

The input output interface 305 comprises a voltage sensor 455 which measures the voltage of the signal provided by the signal conditioner 452 to the electromechanical transducers T5 to T8.

The sensed current and voltage are provided to an analogue to digital converter ADC 451.

Figure 5:
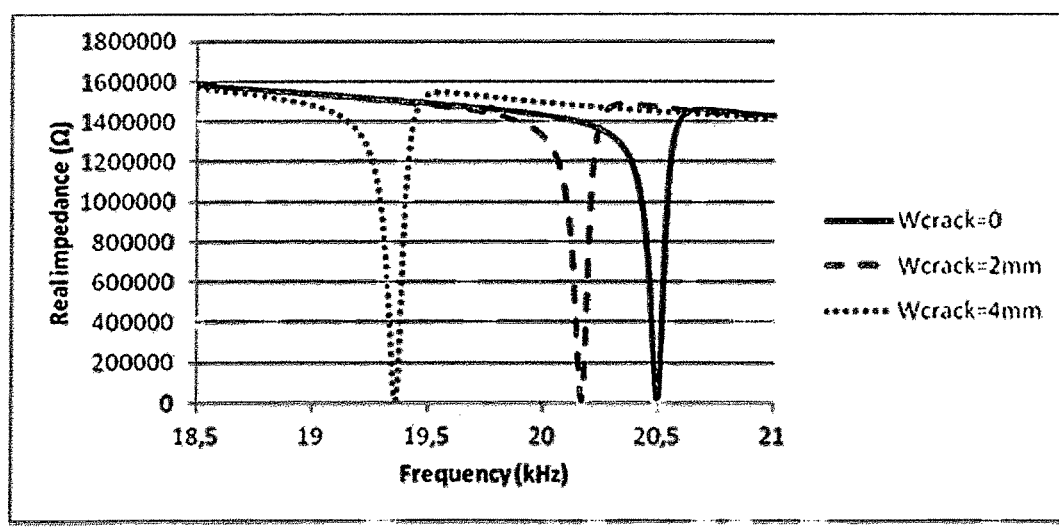
FIG. 5 represents examples of impedance variations of an electromechanical transducer according to the existence of deterioration in at least one interface of the electric power module.

FIG. 5 represents examples of impedance variations of an electromechanical transducer according to the existence of deterioration in at least one interface of the electric power module.

The horizontal axis represents the frequency range of the signal provided by the signal conditioner 402 or 452 and the vertical axis represents the real part of the impedance of the electromechanical transducer.

The impedance of the electromechanical transducer is determined by the processor 300 from the measured voltage and currents.

The bold curve represents the impedance variations of the electromechanical transducer when there is no deterioration in one interface of the sensed die.

The long dotted curve represents the impedance variations of the electromechanical transducer when there is a deterioration, more precisely a crack, of 2 mm in one interface of the sensed die.

The short dotted curve represents the impedance variations of the electromechanical transducer when there is a deterioration, more precisely a crack, of 4 mm in one interface of the sensed die.

FIG. 6 represents an example of an algorithm executed by the deterioration monitoring device according to the present invention.

More precisely, the present algorithm is executed by the processor 300.

At step S60, the processor 300 determines if it is time to perform a measurement of the impedance of the electromechanical transducer T.

If it is time to perform a measurement of the impedance of the electromechanical transducer, the processor 300 moves to step S61.

For example, the processor 330 determines that it is time to perform a measurement of the impedance of the electromechanical transducer based on information relative to parameters such as the time elapsed since the last impedance measurement and/or the number of stress cycles, defined as temperature variations of vibrations, since the last impedance measurement, the temperature of the die, the level of vibration of the die is subject to and/or the state, in operating mode or idle mode, of the electric power module or simply at each power-up of the processor 300.

For example, the processor 300 determines that it is time to perform a measurement of the impedance of the electromechanical transducer, every day, when the temperature of the electric power module is known and stable and/or in the absence of external vibrations.

For example, when the electric power module is included in an offshore windmill, the impedance measurement is performed every time the windmill is stopped, if the number of stress cycles since last measure is greater than a predefined threshold value.

When it is the time to perform a measurement procedure, the processor 300 commands the input output interface 305 in order to perform a measurement procedure.

At step S61, the processor 300 starts a measurement procedure. The measurement procedure may be the generation of a single signal at a predetermined frequency. The predetermined frequency is for example at the resonant frequency of the electromecanical transducer placed in the electric power module and wherein no deterioration exists in the interface or is at the resonant frequency of the electromecanical transducer placed in the electric power module and wherein a deterioration of a predetermined distance exists in one interface. The single signal may be a measurement performed one time or N times, with N>1, spaced by a predetermined duration.

The measurement procedure may be the generation of plural signals at different frequencies. The frequencies cover a frequency range of that is representative of the different possible resonant frequencies of the electromechanical transducer. The measurements on the frequency range may be executed one times or N times, with N>1, spaced by a predetermined duration. When plural dies are monitored by a single electromechanical transducer, the measurement procedure is executed simultaneously for each die.

When plural dies are monitored by plural electromechanical transducers, the measurement procedure is executed sequencially for each die. The signals may be sinewaves.

If measurements are performed N times, the processor 300 then reduces the statistical sampling with a function such as the mean or the median function. If the statistical sampling shows a high level of discrepancies, like a wide statistical distribution, the processor 300 may order the generation of a new measurement procedure.

At next step S62, the processor 300 obtains information related to damage, i.e. the presence of deteriorations and eventually the width of the deterioration.

If measurements are performed N times and the statistical sampling shows a high level of discrepancies, like a wide statistical distribution, the processor 300 may determine that the measurements are not reliable and may return to step S60 or the processor 300 commands the notification means to indicate the unreliablity of the measurement.

In order to obtain information related to damage, the processor 300 performs a data processing.

The processor 300 determines the impedance of the electromechanical transducer at a single frequency or at plural frequencies according to measurement step.

The processor 300 may determine the real part of the impedance of the electromechanical transducer at a single frequency or at plural frequencies according to measurement step.

The processor 300 compares the determined impedance to an initial impedance measurement of the electric power module in its healthy state. The initial impedance may be obtained during the first execution of the present algorithm or may be obtained each time a maintenance inspection/ action is performed on the electric power module.

Plural initial impedances may be obtained at different temperatures. The processor 300 selects the initial impedance which corresponds to the temperature of the electric power module when the measurement procedure at step S61 is performed.

The comparison may be a quadratic distance such as the root mean square deviation or the distance metric used to compare the measured impedance to the initial impedance is a modified Kullback-Liebler function as disclosed in the paper of S. Kullback, *Information theory and statistics*, John Wiley and Sons, N Y, 1959 or a cross-correlation function, or a mean absolute percentage deviation function, or a covariance change function.

The processor 300 compairs the distance between the determined impedance and the initial impedance is compared to a threshold value. If the distance is higher than the threshold, a deterioration exists in an interface of the electric power module.

At next step S63, the processor 300 checks if a notification needs to be performed.

A notification has to be notified when the distance is higher than the threshold.

If a notification needs to be performed, the processor 300 moves to step S64. Otherwise, the processor 300 returns to step S60 and another measurement will be performed later.

At step S64, the processor 300 commands the notification means in order to notify that a damage occurred in at least one die of the electric power module.

In a variant a remaining lifetime is computed, for example by using a linear extrapolation of the calculated deterioration mathematical distance between the predetermined and the measured impedance value evolution through time, and where the remaining lifetime is obtained by computation of the crossing point between the extrapolated curve of distance and a distance threshold.

Naturally, many modifications can be made to the embodiments of the invention described above without departing from the scope of the present invention.

The invention claimed is:

1. System for determining if a deterioration occurs in an interface of a semiconductor die of an electric power module, the electric power module further comprising a substrate and at least one electromechanical transducer, the semiconductor die and the at least one electromechanical transducer being placed on or embedded within the substrate, the semiconductor die being interconnected to the substrate through interfaces, wherein the system comprises an input output interface and a processor:

wherein the input output interface:
    transfers at least one electric AC signal to the at least one electromechanical transducer; and
    measures an impedance of the at least one electromechanical transducer, wherein the processor:
    compares the impedance of the at least one electromechanical transducer to a predetermined value; and
    decides that the deterioration occurs in the interface of the semiconductor die according to a comparison result.

2. System according to claim 1, wherein the at least one electric AC signal is transferred to the at least one electromechanical transducer plural consecutive times and in that the processor further performs statistics on measured impedances and to disable the comparing.

3. System according to claim 1, wherein, if statistics show a high level of discrepancies, the processor indicates the unreliability of the measurement.

4. System according to claim 1, wherein the electric power module further comprises a waveguide between the electromechanical device and one semiconductor die.

5. System according to claim 1, wherein the electric power module comprises plural semiconductor dies and a single electromechanical transducer and at least one electric signal is transferred to the single electromechanical transducer.

6. System according to claim 1, wherein the electric power module comprises plural semiconductor dies and one electromechanical transducer for each semiconductor die and at least one electric AC signal is transferred sequentially to each electromechanical transducer, the impedance of each electromechanical transducer is measured and, each measured impedance being compared to one predetermined value and the deciding that the deterioration occurs in one interface is performed according to the comparison result.

7. System according to claim 1, wherein plural electric AC signals at different frequencies covering a frequency range are transferred to the or each electromechanical transducer, the impedance of the or each electromechanical transducer is measured at each frequency.

8. System according to claim 1, wherein only the real part of the impedance is used for the comparison.

9. System according to claim 1, wherein the comparison is performed using a quadratic distance comparison or a cross-correlation function, or a mean absolute percentage deviation function, or a covariance change function.

10. System according to claim 1, wherein the processor decides that the deterioration occurs in the interface of the semiconductor die according to the comparison result further determine a remaining lifetime of the electric power module.

11. System according to claim 10, wherein the remaining lifetime is computed using a linear extrapolation of the deterioration mathematical distance between the predetermined and the measured impedance values evolution through time and by computation of the crossing point between the extrapolation and a distance threshold.

12. Method for determining if a deterioration occurs in an interface of a semiconductor die of an electric power module, the electric power module further comprising a substrate and at least one electromechanical transducer, the semiconductor die and the at least one electromechanical transducer being placed on or embedded within the substrate, the semiconductor die being interconnected to the substrate through interfaces, wherein the method comprises:

- transferring at least one electric AC signal to the at least one electromechanical transducer,
- measuring the impedance of the at least one electromechanical transducer,
- comparing an impedance of the at least one electromechanical transducer to a predetermined value,
- deciding that the deterioration occurs in the interface of the semiconductor die according to a comparison result.

* * * * *